United States Patent [19]

Sherman et al.

[11] Patent Number: 5,713,371

[45] Date of Patent: Feb. 3, 1998

[54] METHOD OF MONITORING CERVICAL DILATATION DURING LABOR, AND ULTRASOUND TRANSDUCER PARTICULARLY USEFUL IN SUCH METHOD

[76] Inventors: Dani Sherman, 10 Nahal Soreq, 47204 Ramat Hasharon; Avner Aduram, Shderot Weizmann, 47211 Ramat Hasharon, both of Israel

[21] Appl. No.: 499,785

[22] Filed: Jul. 7, 1995

[51] Int. Cl.$^6$ ............................................. A61B 5/103
[52] U.S. Cl. ........................... 128/778; 128/774; 128/661.02
[58] Field of Search ............................. 128/774, 778, 128/775, 661.02, 660.01, 660.02, 660.06, 662.03, 662.06, 675, 660.08

[56] References Cited

U.S. PATENT DOCUMENTS

| | | | |
|---|---|---|---|
| 5,034,648 | 7/1991 | Gastgeb | 310/330 |
| 5,111,805 | 5/1992 | Jaggy et al. | 310/334 |
| 5,315,204 | 5/1994 | Park | 310/339 |
| 5,317,229 | 5/1994 | Koehler et al. | 310/334 |
| 5,370,120 | 12/1994 | Oppelt et al. | 128/660.03 |
| 5,406,961 | 4/1995 | Artal | 128/778 |
| 5,438,996 | 8/1995 | Kemper et al. | 128/778 |
| 5,483,963 | 1/1996 | Butler et al. | 128/661.01 |

*Primary Examiner*—Guy V. Tucker
*Assistant Examiner*—Patrick W. Rasche
*Attorney, Agent, or Firm*—Mark M. Friedman

[57] ABSTRACT

A method for monitoring cervical dilatation during labor by attaching an ultrasound transmitter and an ultrasound receiver to opposite sides of the cervix and monitoring the input signal to the ultrasound transmitter and the output signals from the ultrasound receiver to provide a measurement of the distance between the transmitter and receiver. The method is characterized in that the ultrasound transmitter produces a divergent ultrasound beam received by the ultrasound receiver. Also provided is an ultrasound transducer device including a clip having a pair of jaws spring-urged to a close position and an ultrasound transducer mounted to one of the jaws, characterized in that the ultrasound transducer has a piezoelectric transmitter surface producing a divergent ultrasound beam.

7 Claims, 3 Drawing Sheets

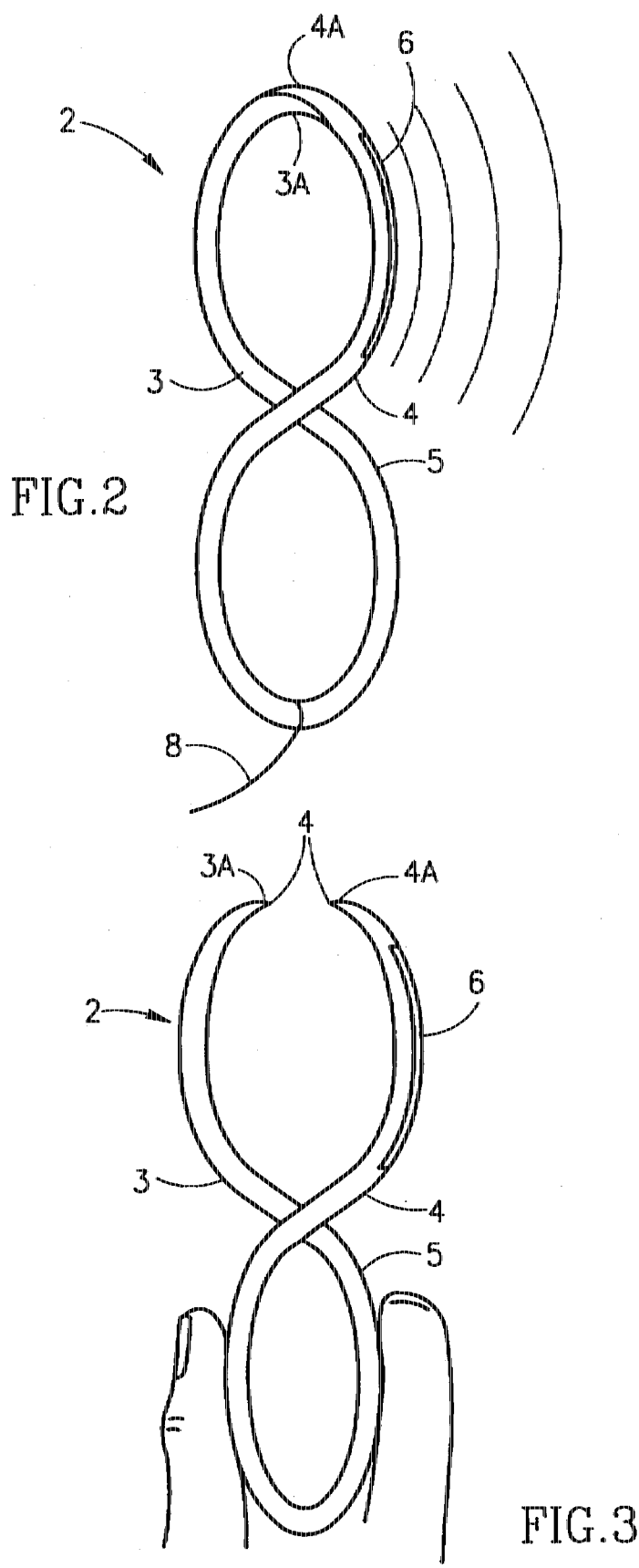
FIG.2
FIG.3
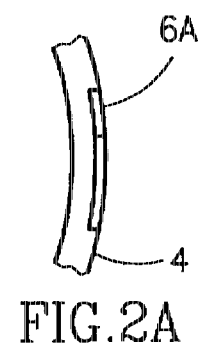
FIG.2A
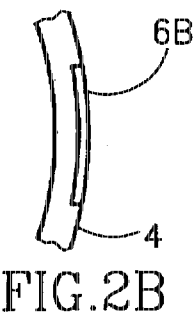
FIG.2B
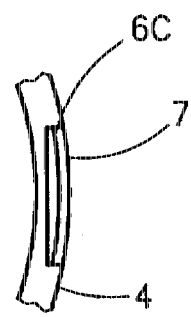
FIG.2C

METHOD OF MONITORING CERVICAL DILATATION DURING LABOR, AND ULTRASOUND TRANSDUCER PARTICULARLY USEFUL IN SUCH METHOD

The present invention relates to a method of monitoring cervical dilatation during labor, and also to an ultrasound transducer particularly useful in such method.

Monitoring cervical dilatation during labor is necessary in order to anticipate and prepare for delivery, and to minimize premature deliveries. At the present time, the common technique for the determination of cervical dilatation and fetal descent in labor is by digital palpation or "digital cervimetry". While this is a quick and simple technique, it has a number of serious limitations, including: non-continuous or intermittent sampling; patient discomfort, directly related to the frequency of sampling; and risk of intrauterine infection, also directly related to the frequency of sampling.

Various techniques have been previously proposed for continuous monitoring of cervical dilatation. These include various types of mechanical, electro-mechanical, pneumatic and electromagnetic devices, but these types of devices suffer from a number of disadvantages and never gained widespread use.

It has also been proposed to use ultrasound transducers, in which an ultrasonic signal transmitted by one transducer attached to one side of the cervix is received by an ultrasound receiver attached to the opposed side of the cervix. Such a technique monitors the input signal to the ultrasound transmitter and the output signal from the ultrasound receiver to provide a measurement of the distance between the two. One such technique is described by Zador et al. in 1974, utilizing crystal-type piezoelectric transducers carried by spring-loaded clips attached to the rim of the cervix. (Zador, I., Neuman, M. R., Wolfson, R. N., "Continuous Monitoring of Cervical Dilatation During Labor by Ultrasonic Transmit-Time Measurement", M. Ed. Biol., B. Engin. 1976; 14:299–305; and Zador, I., Wolfson, R. N., Neuman, M. R., "Ultrasonic Measurement of Cervical Dilatation during Labor", Ann. Conf. Engin. Med. Biol. 1974; 16:187). A similar cervimeter was presented by Kok et al. in 1976 (Kok, F. T., Wallenberg, A. C., Wladimiroff, J., "Ultrasonic Measurement of Cervical Dilatation During Labor", Am. J. Obstet. Gynecol. 1976; 126:288–290) in which ultrasound transducers including piezoelectric discs mounted in stainless steel cylinders were attached by steel coils screwed into the rim of the cervix. Such ultrasound cervimeters, however, have also not gained widespread use, probably because of the severe alignment problems in the cervimeter of Zador et al., and the large volume and cost in the cervimeter of Kok.

An object of the present invention is to provide a novel method of monitoring cervical dilatation during labor. Another object of the invention is to provide an ultrasound transducer construction particularly useful in such method.

According to one aspect of the present invention, there is provided a method of monitoring cervical dilatation during labor by attaching an ultrasound transmitter and an ultrasound receiver to opposite sides of the cervix, and monitoring the input signal to the ultrasound transmitter and the output signals from the ultrasound receiver to provide a measurement of the distance between the transmitter and receiver; characterized in that the ultrasound transmitter produces a divergent ultrasound beam received by the ultrasound receiver.

According to several described embodiments, the transmitter has a transmitter surface which is convexly curved to produce the divergent ultrasound beam.

In one described embodiment, the transmitter surface includes a flexible plastic film piezoelectric transducer bonded to a convexly-curved substrate; particularly good results are obtainable when the flexible plastic film piezoelectric transducer is a polarized homopolymer of polyvinylidene fluoride (PVDF).

In another described embodiment, the transmitter surface includes a convexly-curved piezoceramic transducer bonded to a substrate.

In a third described embodiment, the transmitter has a transmitter surface which has a planar piezoelectric transmitter surface and a diverging acoustic lens thereover.

According to a further feature in the above described embodiments, the ultrasound transmitter and the ultrasound receiver each includes a clip having a pair of jaws spring-urged to a closed position, at least one of the jaws in one clip including the ultrasound transmitter, and at least one of the jaws in the other clip including the ultrasound receiver.

In practical terms, each ultrasound device could be both a transmitter and a receiver; also, more than two such devices could be used for better accuracy.

According to another aspect of the present invention, there is provided an ultrasound transducer device including a clip having a pair of jaws spring-urged to a closed position, and an ultrasound transducer mounted to one of the jaws; characterized in that the ultrasound transducer has a piezoelectric transmitter surface producing a divergent ultrasound beam.

Further features and advantages of the invention will be apparent from the description below.

BRIEF DESCRIPTION OF THE DRAWINGS

The invention is herein described, by way of example only, with reference to the accompanying drawings, wherein:

FIGS. 2 and 3 more particularly illustrate the ultrasound device shown in FIG. 1, the device being illustrated in its closed condition in FIG. 2 and its open condition in FIG. 3;

FIG. 2a is a fragmentary view illustrating the piezoelectric transducer layer carried by the clip;

FIGS. 2b and 2c are similar fragmentary views as FIG. 2a but illustrating variations in the construction of the piezoelectric transducer;

Figure 1:
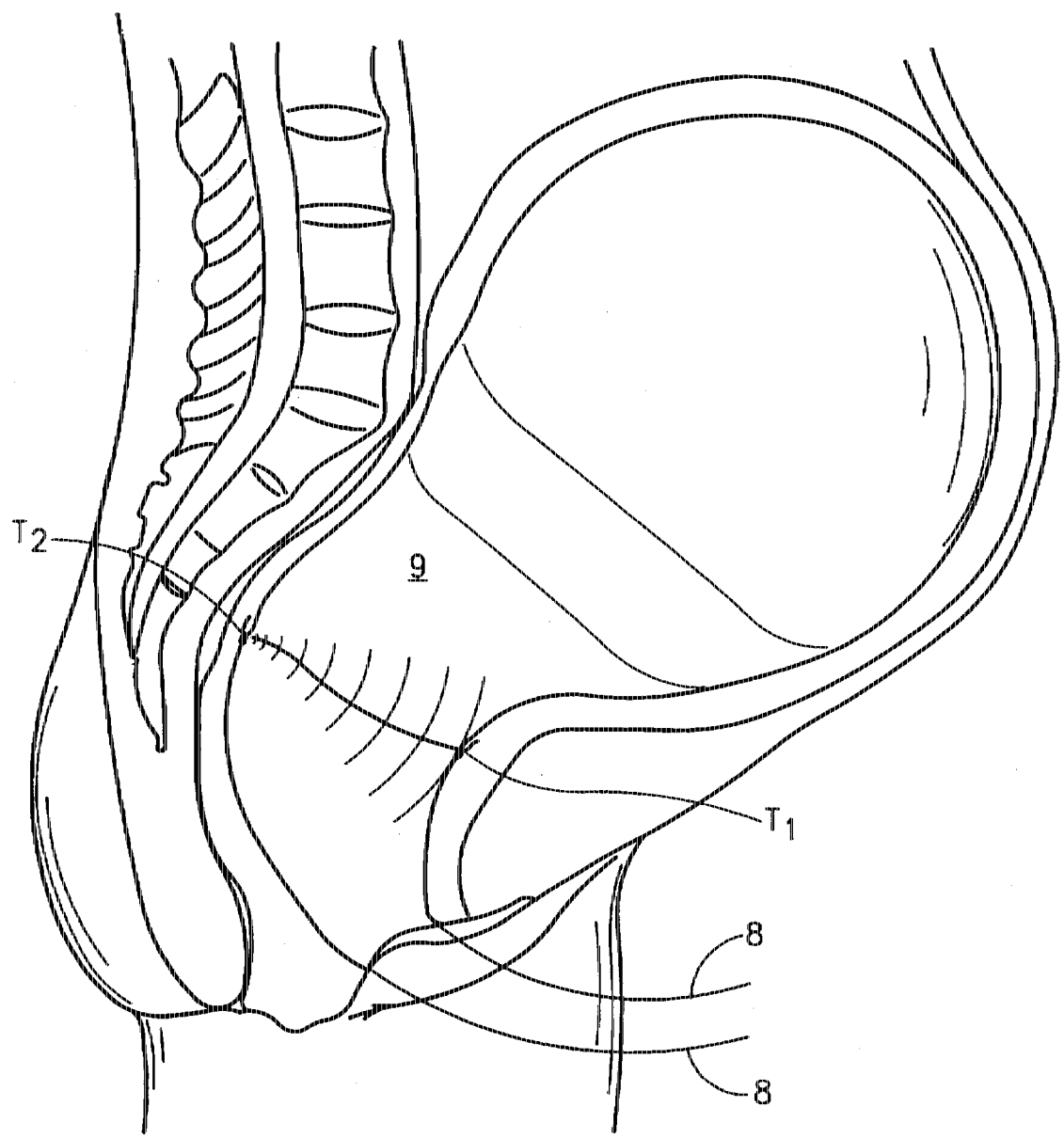
FIG. 1 pictorially illustrates a uterus and cervix during normal labor, with the novel sound transducers applied to monitor cervical dilatation in accordance with the present invention.

With reference first to FIG. 1, this figure illustrates a uterus and cervix during normal labor. For purposes of monitoring cervical dilatation, a first ultrasound transducer device $T_1$ is attached to one side of the rim of the cervix, namely the lateral rim of the external cervical os, and a second ultrasound transducer device $T_2$ is attached to the opposite side of the cervical rim. Transducer $T_1$ is attached at the 3 o'clock position, and transducer $T_2$ is attached at the 9 o'clock position.

FIGS. 2 and 3 more particularly illustrate the construction of each of the two ultrasound transducer devices $T_1$, $T_2$. Preferably, they are both of the same construction, and each may function either as a transmitter or as a receiver.

As shown in FIGS. 2 and 3, each transducer device includes a clip, generally designated 2 of a figure-8 configuration, including a pair of jaws 3, 4 at one side, and a spring loop 5 at the opposite side, urging the two jaws to their closed positions as illustrated in FIG. 2. A squeezing pressure applied to the spring loop 5 will cause the jaws to open, as shown in FIG. 3. The outer tips of the jaws 3, 4 are sharpened, as shown in 3a and 4a, to enable them to penetrate the tissue to which the clip is applied.

Jaw 4 of the clip is provided with a piezoelectric transducer 6. Preferably, transducer 6 is a flexible plastic film having piezoelectric properties, and is bonded to the convexly-curved surface of jaw 4 so that it too assumes a convex curvature. Accordingly, the transducer, when used as a transmitter, transmits a divergent ultrasonic beam. Other curved surface shapes could be used, such as cylindrical, spherical or a combination thereof.

Assuming that transducer $T_2$ in FIG. 1 is the transmitter, and transducer $T_1$ is the receiver, it will be seen that the divergent transmitted beam will enable the receiver to receive the beam even in the presence of misalignment between the transmitter and the receiver. Accordingly, the use of such transducer devices greatly reduces the misalignment problems heretofore experienced in the previously-used ultrasonic transducers for monitoring cervical dilatation, as described for example in the above-cited reference of Zador et al.; it also enables transducer devices of much smaller volume and cost to be used as compared to the above-cited Kok cervimeter.

Preferably, the flexible plastic film piezoelectric transducer 6 is of a polymerized homopolymer of polyvinylidene fluoride (PVDF). Such materials are commercially available.

Instead of using a flexible plastic film as a piezoelectric transducer as shown in FIGS. 2 and 2a, there may also be used a piezoceramic transducer, but in this case the transducer is processed to have the curved convex surface. Such a construction is illustrated in FIG. 2b, wherein it will be seen that the ceramic transducer, therein designated 6b, is shaped to conform to the convex surface of jaw 4 of the mounting clip 2.

FIG. 2c illustrates a further manner of producing the divergent beam. In this case, a planar type ceramic transducer 6c is mounted to the convex surface of the clip jaw 4, but an acoustic lens 7 is applied to the outer face of the transducer to thereby produce the divergent ultrasonic beam.

Before applying the ultrasonic transmitter $T_1$ and receiver $T_2$, the patient is prepared for an aseptic vaginal examination in lithotomic position. The two ultrasonic devices, each carried by one of the clips 2 illustrated in FIGS. 2 and 3, are introduced into the vagina, direct against the lateral rim of the external cervical os, and attached to the tissue at the 3 o'clock and 9 o'clock positions, as illustrated in FIG. 1. The ultrasonic transducers of the two devices $T_1$, $T_2$ are connected by electrical wires 8 to a measuring circuit as illustrated in FIG. 4.

Figure 4:
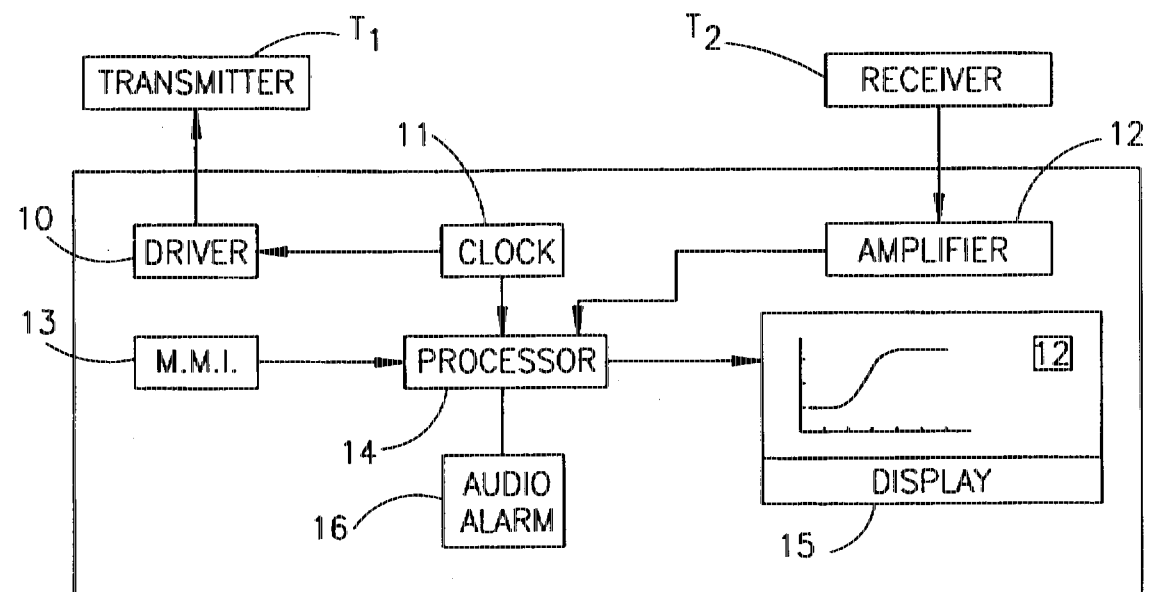
FIGS. 4 and 5 are block diagrams illustrating two electrical measuring systems which may be used with the transducer devices of FIGS. 1–3 for continuously monitoring cervical dilatation during labor.

The measuring circuit illustrated in FIG. 4 includes a driver 10 for driving the transmitter $T_2$, and a clock 11 for triggering the driver. The ultrasonic beam transmitted by the transmitter $T_2$ is received by the receiver $T_1$ and amplified in an amplifier 12.

The system illustrated in FIG. 4 further includes a man-machine interface (MMI) unit 13 which is used for programming a processor 14. The processor receives the clock signal from the clock unit 11, and driving the transmitter $T_2$, and also the amplified signal of the ultrasonic receiver $T_1$ via the amplifier 12. From this information, the processor 14 can calculate the distance between the transmitter $T_2$ and receiver $T_1$, which is the same as the cervical dilatation (minus a known geometrical constant).

This distance is displayed within the display 15, in graphical and/or alphabetical form, and is also sent to an audio alarm unit 16 for actuating the alarm when a predetermined cervical dilatation is found to be present.

As indicated earlier, the ultrasonic transducers $T_1$, $T_2$ can function interchangeably as a transmitter or receiver. More than two transducers (e.g., three or more) can be used when greater accuracy is needed.

The piezoelectric transducers also serve as tactile sensors for sensing the moment of fetal arrival at the cervical os site.

Figure 5:
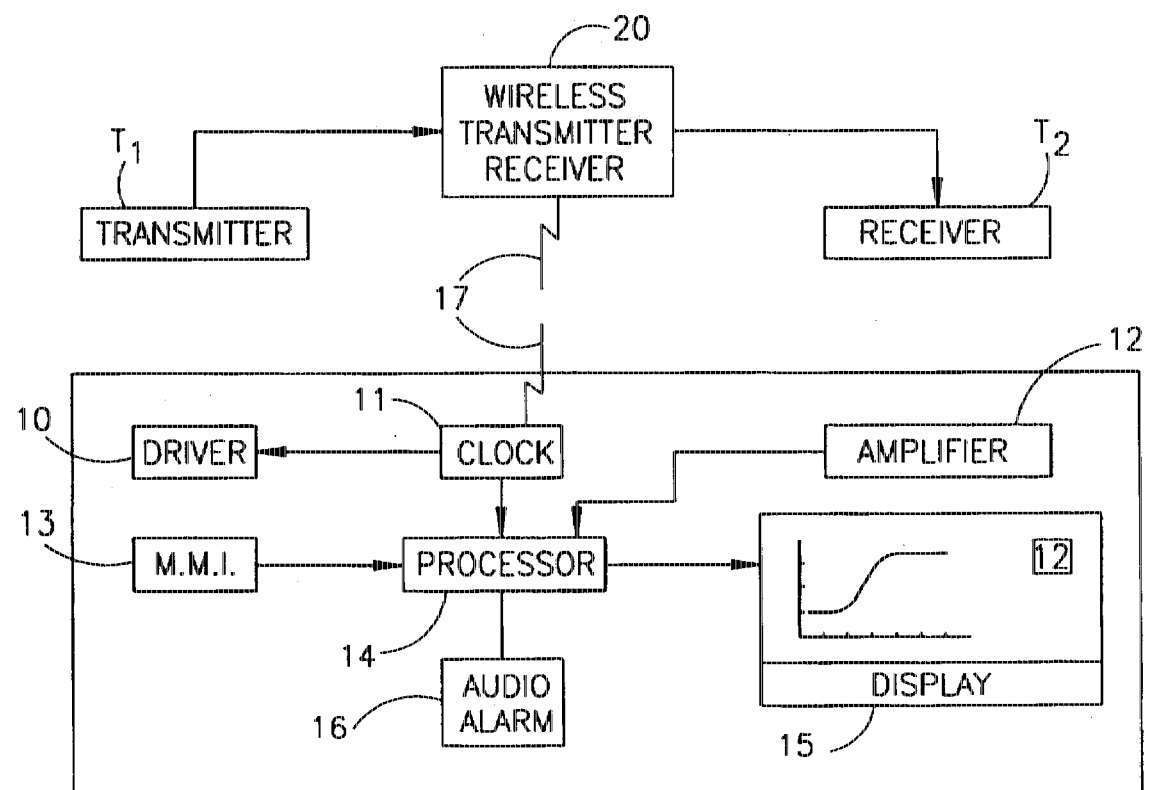

Further, instead of using a wire connection from the ultrasonic transducers within the vagina to the external measuring system, a wireless connection may be used. This is shown in the block diagram of FIG. 5, wherein the coupling between the two transducers $T_1$, $T_2$ within the vagina to the external measuring circuit is effected by a wireless transmitter/receiver unit 20 which has a wireless coupling, e.g. radio frequency (RF) or infrared (IR), with the measuring circuit. The remainder of the measuring system is otherwise the same and operates in substantially the same manner, as described above.

While the invention has been described with respect to several preferred embodiments, it will be appreciated that these are set forth merely for purposes of example, and that many other variations, modifications and applications of the invention may be made.

We claim:

1. A method of monitoring cervical dilatation during labor by attaching an ultrasound transmitter and an ultrasound receiver to opposite sides of the cervix, wherein each said ultrasound transmitter and said ultrasound receiver includes a clip having a pair of jaws spring-urged to a closed position, at least one of said jaws in one clip including said ultrasound transmitter, and at least one of said jaws in the other clip including the ultrasound receiver, and monitoring the input signal to the ultrasound transmitter and the output signals from the ultrasound receiver to provide a measurement of the distance between said transmitter and receiver; characterized in that the ultrasound transmitter produces a divergent ultrasound beam received by the ultrasound receiver.

2. The method of claim 1, wherein said transmitter has a transmitter surface which is convexly curved for producing said divergent ultrasound beam.

3. The method of claim 1, wherein said transmitter surface includes a flexible plastic film piezoelectric transducer bonded to a convexly-curved substrate.

4. The method of claim 3, wherein said flexible plastic film piezoelectric transducer is a polarized homopolymer of polyvinylidene fluoride (PVDF).

5. The method of claim 1, wherein said transmitter has a transmitter surface which includes a convexly-curved piezoelectric transducer bonded to a substrate.

6. The method of claim 1, wherein said transmitter has a planar piezoelectric transmitter surface and a diverging acoustic lens thereover.

7. The method of claim 1, wherein said transmitter includes a convexly curved substrate and a transmitter surface attached thereto.

* * * * *